United States Patent [19]

Wedlock et al.

[11] Patent Number: 5,665,369
[45] Date of Patent: Sep. 9, 1997

[54] FAST-DISPENSING SOLID PVP-CONTAINING CROP PROTECTION FORMULATION AND PROCESS THEREFOR

[75] Inventors: David John Wedlock, Bunbury nr. Tarporley, United Kingdom; Gerhard De Lind Van Wijngaarden, The Hague, Netherlands

[73] Assignee: American Cyanamid Company, Madison, N.J.

[21] Appl. No.: 406,988

[22] PCT Filed: Oct. 6, 1993

[86] PCT No.: PCT/EP93/02770

§ 371 Date: May 23, 1995

§ 102(e) Date: May 23, 1995

[87] PCT Pub. No.: WO94/08455

PCT Pub. Date: Apr. 28, 1994

[30] Foreign Application Priority Data

Oct. 8, 1992 [EP] European Pat. Off. ........... 92309173.0

[51] Int. Cl.$^6$ .................................................. A01N 25/12
[52] U.S. Cl. ...................... 424/408; 424/405; 424/409; 424/419

[58] Field of Search ....................... 424/408, 406, 424/405, 409, 417, 419

[56] References Cited

U.S. PATENT DOCUMENTS

| | | | |
|---|---|---|---|
| 4,801,460 | 1/1989 | Goertz et al. | 424/465 |
| 5,006,595 | 4/1991 | Smith et al. | 524/548 |
| 5,073,379 | 12/1991 | Klimesch et al. | 424/467 |
| 5,180,587 | 1/1993 | Moore | 424/408 |

FOREIGN PATENT DOCUMENTS

| | | |
|---|---|---|
| 3247918 A1 | 6/1984 | Germany . |
| 2178658A | 2/1987 | United Kingdom . |
| 2249957 | 5/1992 | United Kingdom . |

*Primary Examiner*—Neil S. Levy
*Attorney, Agent, or Firm*—Joseph M. Mazzarese

[57] ABSTRACT

A process for producing a solid formulation of a crop protection agent which has an exceptionally fast rate of dispersion in water, and the formulation made by this process. This process includes coextruding a crop protection agent and polyvinylpyrrolidone, and subsequently cooling and milling the extrudate. The resulting granules may be pressed into tablets or agglomerated into larger granular masses.

10 Claims, No Drawings

FAST-DISPENSING SOLID PVP-CONTAINING CROP PROTECTION FORMULATION AND PROCESS THEREFOR

The present invention relates to crop protection formulations which are in solid form, for example powder, granules or tablets.

Crop protection agents are formulated in solid or liquid compositions, usually in the form of a concentrate for ease of handling and transportation, which is diluted with water by the user before application. Often a surface active agent is required to facilitate dilution and is incorporated into the formulation.

Liquid formulations in the form of emulsifiable concentrates contain a very high proportion of organic solvent (often up to 80 percent) which are increasingly coming under scrutiny for their effect on the environment; emulsion concentrates have a higher water content but still contain organic solvents. Suspension concentrates, another water-based liquid form, are often viscous giving rise to handling problems and loss of active ingredient through retention in the packaging.

Solid formulations can also have disadvantages; the more common granules and powders in particular can be difficult to measure but more importantly can be dusty and pose inhalation hazards for the formulator and the user. Tablets have not been used extensively because they are often slow to dissolve. In addition, solid formulations have been found generally to possess a lower biological activity than liquid formulations. Also, with unsophisticated mixing techniques at the site of use, usually in a farmer's field, the tendency of solid forms not to disperse immediately can cause not only clogging of spray equipment with undispersed formulation, but also an inadequate application of active ingredient to the crop to be treated.

Thus there is a need for a fast-dispersing solid crop protection formulation which has better handling characteristics and enhanced biological activity over conventional forms, to satisfy both environmental concerns and provide an effective, product for the farmer to use in an unsophisticated manner in the field.

The Applicants have found that a solid formulation prepared by coextruding a crop protection active ingredient with polyvinylpyrrolidone, and subsequently cooling and milling the extrudate, has an exceptionally fast rate of dispersion in water, and maintains the full biological potential of the crop protection active ingredient. For even greater ease of handling, the granular product may be pressed or compacted into tablet form, or agglomerated into larger granular masses.

Polyvinylpyrrolidone (PVP) has been used extensively in the pharmaceutical industry as a binder or carrier for pharmaceutically active ingredients, especially to assist dissolution and use of sparingly soluble active materials. When used as the base matrix for solid solutions, the conventional preparation method is by solvent evaporation: the active component and PVP are dissolved together in a suitable organic solvent and then the solvent is evaporated off to leave the solid in an amorphous form. The drying stage and the solvent recovery (to avoid contamination of the environment) are difficult and expensive processing steps.

There has been little incentive to utilise PVP in the crop protection industry because the dispersion problems have hitherto been resolved by the use of surface-active/emulsifying agents.

Furthermore there is a prejudice against using PVP at the high temperatures generated by extrusion. Technical Bulletin 2550-006 of GAF (Great Britain) Limited, now known as ISP Europe Ltd, entitled "PVP Polyvinylpyrrolidone-physical, chemical physiological and functional properties" advises that exposure to extreme elevated temperatures should be avoided.

The book entitled "PVP-A Critical Review of the Kinetics and Toxicology of Polyvinylpyrrolidone (Povidone)" by Robinson, Sullivan and Borzelleca also notes:

"Under ordinary conditions, PVP is stable as a solid and in solution. The solid tolerates heating in air for 16 hours at 100° C., but darkening and loss in solubility occurs at 150° C."

Because of the apparent tendency to decomposition, the use of PVP, and related polymers, were ruled out as thermoplastic carriers for medicines.

U.S. Pat. No. 4,801,460 proposes the use of specific forms of PVP in injection moulding or extrusion with a pharmaceutical active ingredient but warns that melting or softening below a certain temperature is necessary to avoid possible thermal and/or oxidative damage to the polymer, and proposes extrusion temperatures should especially be below 130° C. The process disclosed also requires the moulding, or extrusion and subsequent shaping, to be carried out at from 50° to 180° C., and suitably yields tablets for controlled release of the active ingredient. Such preparations yield up the active ingredient slowly over time and indeed from the Examples the minimum time of complete release of active ingredient from a tablet prepared by extrusion is 16 minutes; the maximum is 8 hours. This type of solid formulation would be totally unsuitable for use as a solid crop protection formulation, where rapid dispersal on dilution with water is required and expected. U.S. Pat. No. 4,801,460 does briefly indicate that the extrusion process can be adapted to provide rapid release forms—but this is only envisaged as possible by the alteration of the type and amount of the comonomers used to prepare the polyvinylpyrrolidone polymer (Column 5, lines 22 to 25), and no exemplification of such 'buccal' forms is given. It is the Applicants belief that where dry melt extrusion and shaping at elevated temperature of a PVP-based mixture is performed, the resulting tablet will only be suited to sustained release of the active components.

The Applicants have found that using the process of the present invention, surprisingly, a solid formulation is derived from which full release of active ingredient in less than a minute can be achieved. Furthermore, the activity of a solid formulation prepared in this way has been found to be superior to that prepared by a solvent evaporation route, and equal to that exhibited by a standard, commercial emulsifiable concentrate form of the same active ingredient.

Accordingly, the present invention provides a process for the preparation of a solid formulation of a crop protection agent which comprises coextruding an active ingredient with polyvinylpyrrolidone (PVP), subsequently cooling the extrudate until brittle, and then milling.

Milling is a process of, primarily, crushing, grinding and pulverising, which produces minute granules of extrudate. If desired, the milled extrudate resulting from the process of the invention can be pressed (without heating) into tablet form or agglomerated into granules without loss of the rapid dispersal characteristics. If appropriate, inert processing auxiliaries such as surface-active dispersants or wetters, fillers, etc., are mixed with the milled extrudate prior to tabletting or agglomeration.

The cooling of the extrudate should be carried out straight after the extrusion process and may be effected in any suitable, conventional manner. It has been found useful to run the extrudate onto a roller assembly which is cooled, for example by using chilled water or optionally a chilled water-antifreeze mixture. The extrudate is preferably cooled rapidly to a temperature in the range of from 5° to 25° C., especially 10° to 15° C. The extrudate can then be run off or, if necessary, scraped or chipped off, the roller and conveyed direct to suitable milling equipment for example a roll mill or preferably a hammer mill. Using a combined chill roller and roll mill assembly, it may be possible to perform both the cooling and milling operations in one piece of equipment.

Following milling, it is preferable to classify or screen the particulate extrudate, to obtain a particle size which is optimal for use or subsequent processing. Undersized particles could be recycled to the extrusion stage; oversized particles could be recycled to the milling stage.

The milling equipment is suitably such as to achieve particles of a granular consistency, having for example a diameter in the region of 250 micrometers. A solid formulation prepared in this manner has little associated dust once sieve-cut to cause particular handling or product loss problems.

For the extrusion itself, any suitable extrusion equipment may be utilised. Extruders consist, generally, of a cylindrical barrel in which materials are heated and moved through the barrel by means of at least one rotating screw. Thus the action in the barrel is one of shearing, rubbing and kneading at elevated temperature. In this way the active ingredient and the PVP become mixed on a molecular scale and under the combination of externally applied heat and the internal shear force, which creates more internal heat within the mixture, a solid solution of active ingredient in the PVP is formed.

Suitable extrusion equipment is a twin screw, co-rotating extruder, such as is used in the food processing pharmaceutical, and polymer processing industries. Typically extrusion is carried out in a twin screw extruder having a barrel with a cooled feed zone and with at least one melt zone. For two or more melt zones, each melt zone is of a different temperature in accordance with a graduated temperature profile. The melt temperature or temperature profile is suitably such that the extrudate on leaving the extruder barrel has a temperature in the range of from 50° to 200° C. for example from 150° to 200° C., but preferably from 80° to 200° C. There may be several zones in the extruder barrel, for example from 4 to 9, each having a defined temperature usually obtained by the combination of external electrical heating of the barrel, internal shear forces and, if necessary, water cooling. The temperature of the mixed materials within the barrel is often significantly higher than the applied temperature in view of the heat generated by the internal shear force; to maintain a defined temperature for each zone, external cooling, eg by water, as well as heating may be required. The extruder may incorporate a die plate to aid subsequent extrudate processing, but in fact there is no need to have a die place and if, for example, a chill roller or chill roller/mill assembly is also used, it is preferable that there should be no die plate on the machine. The extruder may also incorporate a separate preliminary mixing section, if needed.

With suitable selection of the equipment for the process of the present invention, the formulation operation can be carried out continuously, and naturally on a commercial scale this is preferred.

Any crop protection agent can be formulated by the process of the invention provided that it dissolves in PVP to form a solid solution and does not chemically decompose during extrusion. The temperature profile of the extrusion process will need to be adapted to operate at temperatures compatible with the fusion points of the active ingredient and the PVP. Preferably extrusion is carried out at or especially above the fusion point of the active ingredient/PVP mixture. Furthermore, the amount of active ingredient used will depend on the degree to which it is soluble in the PVP. Exceeding the solubility limit of active ingredient in PVP it is still possible to prepare a solid formulation by the process of the invention but the dispersion and biological characteristics may be impaired. Naturally for each active ingredient, such optimisation of operation temperature and ingredient proportions for the process can be carried out by routine experimentation. Suitably, a crop protection agent having a melting temperature in the range of from 60° to 200° C. is used.

Particular active ingredients that are suited for formulation by the process of the present invention are: insecticides: including pyrethroids for example, 5-benzyl-3-furylmethyl (E)-(1R)-cis-2,2-dimethyl-3-(2-oxothiolan-3-ylidenemethyl)cyclopropanecarboxylate; permethrin (3-phenoxybenzyl(1RS)-cis-trans-3-(2,2- dichlorovinyl)-2,2-dimethylcyclopropanecarboxylate); fenpropathrin ((RS)-α-cyano-3-phenoxybenzyl 2,2,3,3-tetramethylcyclopropanecarboxylate); esfenvalerate ((S)-α-cyano-3-phenoxybenzyl (S)-2(4-chlorophenyl)-3-methylbutyrate); fenvalerate ((RS)-α-cyano-3-phenoxybenyl(RS)-2-(4-chlorophenyl)-3-methylbutyrate); cyfluthrin ((RS)-α-cyano-4-fluoro-3-phenoxybenzyl(1RS)-cis-trans- 3-(2,2-dichlorovinyl)-2,2-dimethylcyclopropanecarboxylate); beta-cyfluthin (a reaction mixture comprising two enantiomeric pairs in approximate ratio 1:2(S)-α-cyano-4-fluoro-3-phenoxybenzyl(1R)-cis-3-(2,2-dichlorovinyl)-2,2-dimethylcyclopropanecarboxylate and (R)-α-cyano-4-fluoro-3-phenoxybenzyl(1S)-cis-3-(2,2-dichlorovinyl)-2,2-dimethylcyclopropanecarboxylate with (S)-α-cyano-4-fluoro-3-phenoxybenzyl (1R)-trans-3-(2,2-dichlorovinyl)-2,2-dimethylcyclopropanecarboxylate and (R)-α-cyano-4-fluoro-3-phenoxybenzyl(1S)-trans-3-(2,2-dichlorovinyl)-2,2-dimethylcyclopropanecarboxylate); lambda-cyhalothrin (a reaction product comprising equal quantities of (S)-α-cyano-3-phenoxybenzyl(Z)-(1R)-cis-3-(2-chloro-3,3,3-trifluropropenyl)-2,2-dimethylcyclopropanecarboxylate and (R)-α-cyano-3-phenoxybenzyl(Z)-(1S)-cis-3-(2-chloro-3,3,3-trifluoropropenyl)-2,2-dimethylcyclopropanecarboxylate); cyhalothrin (RS)-α-cyano-3-phenoxybenzyl(Z)-(1RS)-cis-3-(2-chloro-3,3,3-trifluoropropenyl)-2,2-dimethylcyclopropanecarboxylate); deltamethrin ((S)-α-cyano-3-phenoxybenzyl(1R)-cis-3-(2,2-dibromovinyl)-2,2-dimethylcyclopropanecarboxylate); cypermethrin ((RS)-α-cyano-3-phenoxybenzyl(IRS)-cis-trans-3-(2,2-dichlorovinyl)-1,1-dimethylcyclopropanecarboxylate); and alpha-cypermethrin (a racemate comprising (S)-α-cyano-3-phenoxybenzyl(1R)-cis-3-(2,2-dichlorovinyl)-2,2-dimethylcyclopropanecarboxylate and (R)-α-cyano-3-phenoxybenzyl(1S)-cis-3-(2,2-dichlorovinyl)-2,2-dimethylcyclopropanecarboxylate); organophosphates, for example, chlorfenvinphos (2-chloro-1-(2,4-dichlorophenyl) vinyl diethyl phosphate); mevinphos (methyl 3-(dimethoxyphosphinoyloxy)but-2-enoate) and tetrachlorvinphos ((Z)-2-chloro-1-(2,4,5-trichlorophenyl) vinyl dimethyl phosphate); fenbutatin oxide (bis[tris(2-methyl-2-phenylpropyl)tin]oxide); flufenoxuron (1-[4-(2-chloro-α,α,α-trifluoro-p-tolyloxy)-2-fluorophenyl]-3-(2,6-difluorobenzoyl) urea) and triazamate (ethyl(3-tert-butyl-1-dimethyl carbamoyl-1H-1,2,4-triazol-5-ylthio)

acetate); herbicides including flamprop-M (N-benzoyl-N-(3-chloro-4-fluorophenyl)-D-alanine; its isopropyl ester—isopropyl N-benzoyl-N-(3-chloro-4-fluorophenyl)-D-alaninate; and methyl ester—methyl N-benzoyl-N-(3-chloro-4-fluorophenyl)-D-alaninate and cyanazine (2-(4-chloro-6-ethylamino-1,3,5-triazin-2-ylamino)-2-methylpropionitrile); and fungicides including triforine (N,N'-[piperazine-1,4-diylbis[(trichloromethyl)methylene]]diformamide); aldimorph and dimethomorph ((4-[3-(4-chlorophenyl)-3-(3,4-di-methoxyphenyl)acryloyl] morpholine (Z to E ratio normally 4:1)).

In the pyrethroid category, alphacypermethrin in particular may be formulated with PVP by extrusion. For alpha-cypermerthrin as active ingredient, the percent content in the solid formulation may be in the range of from 0.1 to 40% mass by mass (m/m). Preferably in the range of from 30 to 35 % m/m is utilised.

The active ingredient may be used in solid or liquid form. If liquid, the active ingredient can be dosed into the extruder through a liquid feed port.

PVP is a well known commercial product available in various forms from, for example, the companies BASF and ISP; the water-soluble polymer and its preparation is described in, inter alia, The Merck Index, 11th Edition, Monograph 7700. Suitable PVP polymers for use in the present invention are any of the available forms, without restriction. Desirably they have a Fikentscher K value, see U.S. Pat. No. 2,706,701 or Cellulose-Chemie 13 (1932), pages 58 to 64 and 71 to 64, of in the range of from 10 to 100 reflecting a molecular weight of from 5,000 to 700,000. Preferred PVP polymers have a K value of 20 to 40, especially 25 to 35. The polymer is desirably a homopolymer of vinylpyrrolidinone monomers, but may be used as a copolymer provided that at least 50% or more of the polymer units are vinyl pyrrolidinone monomers.

The PVP may be made in any conventional manner, for example by polymerisation initiated by hydrogen peroxide or an organic peroxide in a suitable solvent such as water or a suitable organic solvent.

Naturally the PVP must fuse at the operating temperature of the extruder, and it may be necessary to select a compatible PVP based on the melting point of the active ingredient and the consequent extrusion temperature required. For extrusion with the active ingredient, alpha-cypermethrin, "Agrimer 30" a PVP polymer available from ISP has been found to be very suitable. Agrimer 30 has a K value of 30. This PVP has a glass transition temperature of 156° to 157° C.; when mixed with alpha-cypermethrin, which has a melting point of 77° C., a typical glass transition temperature of the mixture is of the order of 146° C. A suitable operating extrusion temperature or temperature profile for such mixtures is such that the extrudate is a melt having a temperature of above 77° C. and desirably above 110° C. (as determined by routine experimentation); such mixtures have been satisfactorily extruded up to 185° C.

PVP prepared by polymerisation in water may often have a higher water content (of the order of 5% by weight); PVP prepared by other means can also imbibe water from the atmosphere because of its hygroscopic nature. Whereas by the process of U.S. Pat. No. 4,801,460 it is essential to use NVP (another acronym for PVP) which has a water content not exceeding 3.5% by weight because "higher water contents are harmful in that evaporation of the water after the polymer/active compound extrudate emerges from the die results in porous mouldings or may even produce mouldings possessing cracks in the surface", the processing of the extrudate required by the present invention means that the water content of the PVP is not critical. Should PVP having a water content of greater than say 3.5% by weight be used, and it is desired to have a low residual water content in the extrudate, it is a further preferred feature of the present invention that water vapour is drawn off under vacuum, for example by means of a vacuum pump, during extrusion. Thus, preferably, an extruder is used which has one or more vent ports, to vent moisture, associated with a vent port stuffer, to prevent loss of solid material through the vent port, and a vacuum pump to remove water vapour.

If necessary, other ingredients may be co-extruded with the active ingredient and PVP. Thus, additional active ingredients or processing auxilliaries, for example, conventional plasticizers such as urea, glycerol, or N-methyl-2-pyrrolidone, may also be used. Any additional ingredients will depend on the end use of the formulation and/or the main extrusion ingredients. Thus, for example, for extrusion of alpha-cypermethrin technical material, which is a racemic mixture of two cis-2-isomers, the extrusion material must be rendered slightly acidic to prevent epimerisation or inversion of the cis-2-isomers to the cis-1- isomers. Suitably in the range of from 0.5 to 0.9% m/m of an organic acid such as benzoic acid or, preferably, toluene sulphonic acid, is included in the ingredients for extrusion; useful results are also expected from the incorporation of water soluble salts such as potassium hydrogen sulphate or sodium sulphate; potassium hydrogen sulphate is especially preferred. The extrusion ingredients may be added together or separately into the extruder. Conveniently a mixture or blend of the ingredients is used as the extruder feed.

The following Examples illustrate the invention. FASTAC is a registered trade mark for alpha-cypermethrin and is particularly a racemate comprising (S)-α-cyano-3-phenoxybenzyl(1R)-cis-3-(2,2-dichlorovinyl)-2,2-dimethylcyclopropanecarboxylate and (R)-α-cyano-3-phenoxybenzyl(1S)-cis-3-(2,2-dichlorovinyl)-2,2-dimethylcyclopropanecarboxylate. "m/m" means "mass/mass". TORQUE is a registered trade mark for fenbutatin oxide, and CASCADE is a registered trade mark for flufenoxuron.

EXAMPLE 1

A blend of the following powdered materials was mixed using a cone blender

|  | % m/m |
| --- | --- |
| FASTAC (technical material, from Shell International Chemical Company | 33.0 |
| polyvinylpyrrolidone (PVP), Agrimer 30 from ISP (Europe) Ltd | 66.5 |
| p-toluene sulphonic acid (ex B.D.H. Ltd) | 0.5 |

A sample of 5 kg of blended material was fed into an APV MP2030 twin screw co-rotating extruder, 25:1/L/D (length over diameter). A K-tron T20 volumetric feeder with agitated hopper was used to feed the extruder. The extruder barrel which was electrically heated and water cooled was fitted with a vacuum pump via a vent port for use when a melt seal had formed. The barrel melt zone temperatures (nine in all) were set between 25 and 175 degrees centigrade (beginning to end of barrel).

A vacuum was drawn once a melt seal had formed in order to remove the water vapour that formed in the barrel from the residual moisture content of the PVP. The extruder screws were constructed to give a conveyor section followed by a paddle shearing/mixing section. The extrudate was finally conveyed to the end of the barrel and extruded without a die-plate. The extrudate temperature was monitored. A number of extrusions were performed, the extrudate temperatures measured were in the range of from 80 to 181 degrees centigrade.

In each experimental run the extrudate, which was a viscous thermoplastic melt, was conveyed directly onto a chill roller (chilled with water at 4 degrees centigrade). The extrudate was rapidly cooled to a brittle glassy material on the rollers and removed as chips by pegs rotating near the surface of the larger of the two chill rollers. The chipped material was hammer milled and sieve cut to approximately 250 micrometers. It was then mixed with typical tabletting inerts and compressed to a tablet using a tabletting machine. The extrudate showed no detectable crystalline FASTAC using differential scanning calorimetry (Perkin-Elmer DSC 7 machine) when heated through the normal melting temperature of FASTAC.

FASTAC-PVP solid-solutions prepared both in tablet pre-granule form sieve-cut to about 250 to 500 microns, and in compressed tablet form, were found, using in a Hardy RY15 knap sack spray rig at normal field strength dilution rates with water, to release greater than 80% by mass of the active ingredient in less than 1 minute.

EXAMPLE 2

The biological activity of two solid solutions of FASTAC-PVP and a commercial FASTAC emulsifiable concentrate was compared using larvae of the Egyptian cotton leafworm, *Spodoptera littoralis*.

FASTAC Formulation A was prepared by hot melt extrusion with subsequent milling as described in Example 1 to form a granular composition:

| FASTAC technical material | 333 g |
|---|---|
| polyvinylpyrrolidone, Agrimer 30 | 662 g |
| benzoic acid | 5 g |

FASTAC Formulation B was prepared by dissolving the FASTAC technical material and the PVP in an 80/20 m/m mixture of dichloromethane and methanol, then removing the solvent under vacuum:

| FASTAC technical material | 333 g |
|---|---|
| polyvinylpyrrolidone, Agrimer 30 | 666 g |
| orthophosphoric acid | 1 g |

FASTAC Formulation C was a 100 g/l commercial emulsifiable concentrate.

In order to assess the activity of the formulations in the laboratory but at dosages more appropriate to the field situation, a bioassay using a timed exposure of the test insect to a dried spray deposit was used.

Each formulation was diluted with tap water and solutions prepared equating to dosages of 40, 20 and 10 g ai/ha when applied using a sprayer at a delivery rate of 375 l/ha. Individual treatments were applied to the inner surface of both upper and lower portions of a 9.0 cm diameter petri dish. When spray deposits had dried, ten early 4th instar *S. littoralis* larvae were introduced into the deeper half of the petri dish and the lid added. This ensured that all surfaces with which the larvae may make contact, had been treated. After a 12.5 minute exposure period, the individual sets of larvae were transferred to the untreated environment of a 9.0 cm plastic petri dish in which a disc of chinese cabbage leaf was supplied for food. The percent mortality was assessed after 24 hours. The tests were repeated and the mean value calculated.

The results are given in Table 1 below

TABLE 1

| FASTAC Formulation | Dose g ai/ha | % Mortality Test 1 | Test 2 | Mean |
|---|---|---|---|---|
| A | 40 | 100 | 100 | 100 |
|   | 20 | 100 | 90 | 95 |
|   | 10 | 60 | 30 | 45 |
| B | 40 | 100 | 100 | 100 |
|   | 20 | 90 | 90 | 90 |
|   | 10 | 30 | 10 | 20 |
| C | 40 | 100 | 100 | 100 |
|   | 20 | 90 | 100 | 95 |
|   | 10 | 70 | 80 | 75 |

It was noted that Formulation A produced a very good and a very rapid dispersion on addition to water. Formulation B took, relatively, much longer to disperse owing to the denser nature of the product formed by the solvent evaporation technique.

As can be seen although all give good control at the highest active ingredient (ai) dose level, Formulation B gives inferior control at lower ai levels. Formulation A, the extruded FASTAC-PVP formulation, gives effective control for the main part equal to the solvent-based commercial FASTAC formulation, yet does not require undesirable solvent in its preparation nor as an ingredient.

Similar biological evaluations demonstrated the efficacy of the above formulations against Psylla pyricola on pears.

EXAMPLE 3

PVP formulations of TORQUE, CASCADE and mixtures of TORQUE and CASCADE were prepared by hot melt extrusion with subsequent milling, as described in Example 1, except that the extruder had 7 heating zones, all of which were set at 120° C., and the throughput was about 5 kg/hr. The actual compositions thus extruded were:

D) TORQUE 410 g Empicol LZ 50 g N-methyl pyrrolidone 50 g polyvinylpyrrolidone K 30 q.v. 1 kg E) TORQUE 350 g CASCADE 38 g Empicol LZ 50 g potassium hydrogen sulphate 10 g N-methyl pyrrolidone 50 g polyvinylpyrrolidine K 30 q.v. 1 kg F) CASCADE 400 g Empicol LZ 50 g toluene sulphonic acid 10 g N-methyl pyrrolidone 50 g polyvinyl pyrrolidone q.v. 1 kg Each of the above formulations was evaluated for acaricidal activity against the two-spotted spider mite Tetranychus urticae on French bean by spraying formulations of various dilutions. The percent plant damage was then assessed at 15 or 19 days after treatment (DAT), with the results shown in the following Table 2.

TABLE 2

| Formulation | Dose (ppm a.i.) | % damage | |
|---|---|---|---|
| D) TORQUE | 40 | 1.0 | ⎫ |
|   | 13 | 11.2 | ⎬ at 15 DAT |
|   | 4 | 39.1 | ⎭ |
| E) TORQUE/CASCADE | 40 | 1.0 | ⎫ |
|   | 13 | 26.3 | ⎬ at 15 DAT |
|   | 4 | 52.6 | ⎭ |
| F) CASCADE | 7.5 | 11.2 | ⎫ |
|   | 2.5 | 36.6 | ⎬ at 19 DAT |
|   | 0.75 | 62.1 | ⎭ |

Similar biological evaluations demonstrated the efficacy of the above formulations against Panonychus ulmi mite on apples.

EXAMPLE 4

A PVP formulation of dimethomorph, containing 25% w/w of active ingredient and an anionic surfactant, was prepared by hot extrusion with subsequent milling, as described in Example 1 except that the extruder temperature was set at 165° C. The formulation showed negligible decomposition of active ingredient, and exhibited fungicidal activity comparable with standard commercial dispersible concentrate formulations of dimethomorph.

We claim:

1. A process for the preparation of a solid formulation of a crop protection agent that disperses rapidly in water to release greater than 80% by mass of said agent in less than one minute, which process comprises co-extruding said crop protection agent with polyvinylpyrrolidone, subsequently cooling the extrudate until brittle and then milling, wherein said crop protection agent dissolves in polyvinylpyrrolidone to form a solid solution.

2. A process as claimed in claim 1, in which the milled extrudate is pressed into tablet form or agglomerated into granules.

3. A process as claimed in claim 1, in which the extrudate is cooled to a temperature in the range of from 5° to 25° C.

4. A process as claimed in claim 1, in which the extrusion is carried out in accordance with a melt temperature or a graduated temperature profile such that the extrudate on leaving the extruder barrel has a temperature in the range of from 50° to 200° C.

5. A process as claimed in claim 1 in which water vapour is drawn off under vacuum during extrusion.

6. A process as claimed in claim 1, in said crop protection agent is a pyrethroid, an acyl urea, fenbutatin oxide, or dimethomorph.

7. A process as claimed in claim 1, in which toluene sulphonic acid or potassium hydrogen sulphate is also included as an extrusion ingredient.

8. A process as claimed in claim 1 in which a plasticiser, selected from urea, glycerol, and N-methyl-2-pyrrolidone, is also included as an extrusion ingredient.

9. A solid formulation of a crop protection agent, which formulation disperses rapidly in water to release greater than 80% by mass of said agent in less than one minute, prepared by a process as claimed in claim 1.

10. A solid formulation of a crop protection agent, which formulation disperses rapidly in water to release greater than 80% by mass of said agent in less than one minute, prepared by the process claimed in claim 7.

* * * * *